United States Patent [19]
Kato et al.

[11] Patent Number: 4,485,029

[45] Date of Patent: Nov. 27, 1984

[54] DISINFECTING METHOD AND COMPOSITIONS

[75] Inventors: Kenneth H. Kato, Cottage Grove; Arlene J. Mencke, St. Paul, both of Minn.

[73] Assignee: Minnesota Mining and Manufacturing Company, St. Paul, Minn.

[21] Appl. No.: 591,043

[22] Filed: Mar. 19, 1984

[51] Int. Cl.$^3$ .................. A61K 31/23; A61K 31/235; A61L 13/00; C11D 3/48

[52] U.S. Cl. .................................. 252/106; 134/42; 424/234; 424/312

[58] Field of Search ............... 252/106; 424/234, 312, 424/365

[56] References Cited

U.S. PATENT DOCUMENTS

| | | | |
|---|---|---|---|
| 3,884,826 | 5/1975 | Phares | 252/106 |
| 4,002,775 | 1/1977 | Kabara | 426/532 |
| 4,048,122 | 9/1977 | Sibley | 252/541 |
| 4,067,997 | 1/1978 | Kabara | 424/312 |
| 4,104,187 | 8/1978 | Sibley | 252/106 |
| 4,323,467 | 4/1982 | Fu | 252/106 |
| 4,410,432 | 10/1983 | Lucas et al. | 252/107 |

OTHER PUBLICATIONS

American Pharmacy, vol. NS21, (May, 1981), p. 19.
Orth, D. S., Int'l J. Dermatology, vol. 19, (1980), pp. 504–505.
McCutcheon's Emulsifiers & Detergents, 1983, North American Edition, MC Publishing Co.
Kabara, J. J., "The Medium is the Preservative", Cosmetics & Toiletries, vol. 96, (Mar. 1981), pp. 63–67.
Kabara, J. J., "Multi-Functional Food-Grade Preservatives in Cosmetics", Drug & Cosm. Ind., vol. 125, (1979), pp. 60–76, 140–145.

Primary Examiner—Dennis L. Albrecht
Attorney, Agent, or Firm—Donald M. Sell; James A. Smith; James V. Lilly

[57] ABSTRACT

A composition is disclosed which includes the use of glyceryl monolaurate in combination with one or more other anti-microbial agents and, optionally an organic surfactant as a cleaning, disinfecting and preserving system which must be non-irritating and non-allergenic to body tissues. The composition is effective against a variety of microorganisms within a reasonable period of time, at concentrations that, if desired, can result in a visually clear solution. It is useful in a solution for cleaning, disinfecting and preserving contact lenses.

22 Claims, No Drawings

DISINFECTING METHOD AND COMPOSITIONS

BACKGROUND OF THE INVENTION

The present invention relates to compositions containing glyceryl monolaurate (hereinafter GML) in combination with esters of para-hydroxybenzoic acid and, optionally, one or more organic surfactants. More particularly, this invention relates to the use of such compositions at ambient temperatures to clean, disinfect and preserve contact lenses, surgical or dental instruments, and other devices or formulations which contact sensitive body tissues.

For example, soft contact lenses, such as those made from plastic gel materials like hydroxyethyl methacrylate (HEMA) or its analogues and ethylene glycol dimethacrylate (EGMA) or its analogues, are replacing traditional hard contact lenses as the lenses of choice for many people. Soft lenses are more comfortable to wear than the hard lenses, but they pose a more complex problem than the hard lenses when it comes to care and maintenance. Hard lenses may be cleaned and disinfected relatively easily. Since they do not absorb appreciable amounts of water and aqueous solutions, the use of harsher cleaning and disinfecting agents is not generally a problem.

Soft lenses, on the other hand, require greater care in cleansing and storage. The solutions useful with hard lenses generally are not considered compatible with soft lenses because the soft lenses tend to absorb or concentrate certain constituents of the formulation, which could result in damage to the lens or harm to the eye of the user.

Similarly, soft lenses are more vulnerable to microbial contamination than are hard lenses. The nutritive effect of body fluids, and the protective effect of nicks or imperfections in the soft lens, can serve to augment the growth of microbes.

While it is relatively easy to find anti-microbial agents active against such microbial contaminants, it is more difficult to find an anti-microbial agent that is compatible with soft contact lenses, and more difficult yet to find one that is non-irritating and safe for contact with the human eye.

Anti-microbial agents which are suitable for external contact or even for injection or ingestion are often unsuitable for use in eye care due to the particularly sensitive nature of the tissues in the eye. For example, they might be unsuitable because of direct toxicity to the eye, poor solubility in aqueous vehicles, eye irritation or ocular allergenic effects, absorption or binding by the contact lenses, or chemical interaction with the contact lens or even its plastic lens case.

An anti-microbial agent useful for ocular applications must avoid each of the above problems. It must in particular satisfy two basic requirements, i.e. that it be non-irritating to the eye, and that it be effective against a wide variety of microorganisms. Preferably, it must be effective against a panel of six microorganisms recommended by the U.S. Food and Drug Administration (FDA).

In the past, several attempts have been made to provide solutions which could be used to clean, disinfect and preserve soft contact lenses as well as be non-irritating to the eye, non-allergenic and still effective against a wide variety of microorganisms.

The majority of solutions currently approved by the FDA for use with soft contact lenses contain either no preservative at all, or contain one such as sorbic acid, thimerosal, chlorhexidine or quaternary ammonium compounds. (See, for example, American Pharmacy, Vol. NS21 (1981) p. 19).

Such formulations have various drawbacks associated with them. Chlorhexidine, for example, can be absorbed by the soft lenses and subsequently eluted from the lenses into the eye, possibly causing irritation or burning. In addition, this compound has been shown to cause allergic reactions in certain persons. Similarly, thimerosal, another ingredient used widely in contact lens cleaning and disinfecting solutions, can cause irritation or allergic reactions, probably because it is a mercury-containing compound. Quaternary ammonium compounds have also been found to be irritating to the eye or cause an allergic response in some situations.

The choice of formulations suitable for contact lens cleaning and disinfecting solutions therefore, is limited in large part by the choice of anti-microbial agent or agents employed. While a large number of anti-microbial compounds is known, relatively few can meet the stringent requirements of reasonable concentrations, effectiveness, and lack of harmful side effects necessary in an application as demanding as a cleaning and disinfecting and preserving composition for use with contact lenses.

The present invention provides both a composition and a method for the cleaning, disinfecting and preserving of contact lenses which overcomes the disadvantages associated with currently existing solutions. The composition and method is effective against a wide range of microorganisms within a suitable period of time, and is essentially non-allergenic and non-irritating to the eye. Furthermore, the compositions of the present invention can involve the use of an essentially non-irritating surfactant. While the present invention is particularly useful with soft contact lenses, it is also useful with hard contact lenses such as polymethyl methacrylate lenses or hard gas permeable lenses such as silicone acrylate or cellulose acetate butyrate lenses.

SUMMARY OF THE INVENTION

The present invention provides a method and composition for ambient temperature cleaning, disinfecting and preserving of contact lenses. More particularly, it provides a composition suitable for ophthalmic use for cleaning, disinfecting and preserving contact lenses comprising (a) water;

(b) an effective amount of up to 0.1% by weight of a first anti-microbial agent consisting essentially of a polyol ester having a formula selected from

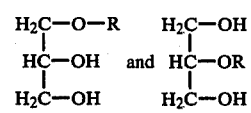

where R is the residue of lauric acid; and (c) an effective amount of a second anti-microbial agent comprising one or more esters of para-hydroxybenzoic acid.

Typically, the solution will be a buffered, isotonic sterile solution which may contain other adjuvants such as EDTA.

One aspect of the invention relates to a composition for cleaning, disinfecting and preserving contact lenses which comprises GML, and one or more complementary anti-microbial agents that give the composition a wide range of microbial activity. Another aspect of the invention relates to one or more surfactants.

Formulations of the invention can be used in a variety of ways, including as a cleaning solution for the immediate removal of proteinaceous material deposited on the lens, a soaking solution which cleans and sterilizes within an overnight period and as a long term storage solution.

As used through this specification, the following terms have the following meanings;

"contact lens" refers particularly to soft and hard contact lenses.

"Suitable for ophthalmic use" means that the material or composition is essentially non-irritating to the eye and has a low allergenic potential for ophthalmic use of the concentrations which are to be used, as measured by standard tests known to the art, such as the Draize eye irritation test, or the Magnusson-Kligman Sensitization Potential test.

"Surfactant" means any organic compound which acts as a wetting, dispersing, emulsifying, solubilizing, foaming or washing agent.

"Complexing agent" refers to a compound which will chemically complex metal ions to inactivate them.

"Anti-microbial agents" includes compounds which are microbicidal, i.e., the ability to kill microorganisms, and/or microbiostatic, i.e., having the ability to inhibit the growth of microorganisms.

"Methyl paraben" is used interchangeably with the methyl ester of para-hydroxybenzoic acid.

"Propyl paraben" is used interchangeably with the propyl ester of para-hydroxybenzoic acid.

DETAILED DESCRIPTION OF THE INVENTION

It has been known to use GML alone or in combination with other microbicides in a microbicidal composition. For example, U.S. Pat. Nos. 4,002,775 and 4,067,997 disclose the use of GML as an anti-microbial agent, and disclose formulations containing GML in combination with phenolic microbicides and ethylenediaminetetraacetic acid (EDTA). These preparations are described as "food-grade microbicides", that is, they are safe for ingested or topical uses. These formulations would not be satisfactory in ocular applications in part, because they necessarily contain such additional chemicals as ethanol in order to keep effective amounts of GML in solution.

Similarly, commercial dry combinations of GML, parabens and EDTA are known such as the product Lauriban TM, available from Med-Chem Laboratories, Monroe, MI. These formulations are neither suitable nor intended for ophthalmic uses however.

Glyceryl monolaurate (GML) has been described in U.S. Pat. Nos. 4,002,775 and 4,067,997. GML is a monoglyceride, i.e. an ester of the trihydric alcohol, glycerol wherein the lauric acid is esterified to either the alpha or beta position of glycerol.

GML has very low solubility in aqueous solution. Most commonly this is not a problem since various means exist for combining GML with other materials to promote its solubility. Such means include solubilizing GML in a solvent which can in turn be dissolved in water, or emulsifying the GML as a suspension of fine droplets within a water phase. Neither the resulting solution nor the resulting dispersion is useful for cleaning, disinfecting and preserving contact lenses.

It was surprising therefore to find that those concentrations of GML in aqueous solution which could in fact be achieved without the aid of such means, included concentrations which were still effective in a microbicidal or microbiostatic sense. It was not expected that one could achieve a concentration of GML in aqueous solution which was effective without the use of some solvent, compound or technique which would simultaneously render that solution incompatible for ophthalmic use. It was further surprising to find that such GML solutions could be combined with effective amounts of other anti-microbial agents in solutions that could be kept optically clear and physically stable and that the resulting solutions could demonstrate effective anti-microbial activity against a variety of microorganisms within a short period of time.

One aspect of the present invention therefore is the discovery that concentrations of GML effective for use with contact lenses can be achieved without the use of chemical means to facilitate its solubility, or physical means to facilitate its suspension. The technique employed in the present invention for solubilizing effective amounts of GML involves essentially forming a stock aqueous dispersion of GML by stirring and heating the solution to 60°–65° C., and using aliquots of this dispersion to form the desired concentration in a solution containing the other ingredients. This technique has been used to achieve stable GML concentrations of up to at least 0.01% by weight, although the more concentrated solutions, e.g. those over about 0.001% are generally hazy or cloudy in appearance.

As indicated, the amount of GML which may be employed in the present invention is limited due to its low solubility in water and the desirability of minimizing the presence of solids which might either deposit on a contact lens, or impart a cloudy appearance to the solution. Surprisingly the maximum amount of GML which is effective in the invention is also limited. Thus it has been found that the amount of GML which is effective should not exceed about 0.1% by weight of the composition. At levels of GML above 0.1%, microbicidal activity is generally not significantly improved yet the solutions will frequently be either cloudy or even suspensions of GML micelles. Preferably the concentration of GML employed to provide microbicidal activity should be in the range of about 0.0001 to 0.1% by weight of the solution. Most preferably, the concentration about 0.0005 to 0.0015% by weight of the solution.

In order to provide a disinfecting solution which has a broad spectrum of microbicidal activity, it is necessary to include components which kill gram-negative bacteria and yeasts, and/or enhance the ability of GML to kill gram-negative bacteria and yeasts. It has been found that esters of para-hydroxybenzoic acit (parabens) are useful in achieving this goal. For example, solutions combining GML and parabens show surprising and unexpected activity against yeast such as *Candida albicans* and fungi such as *Aspergillus fumigatus*. Furthermore, these esters, when combined with GML have been found to provide solutions which are therefore suitable for ophthalmic use.

Parabens are well-known preservatives used most frequently in dermatological medications and cosmetic formulations. (See Orth, D. S., Int'l. J. Dermatol., Vol. 19 (1980) pp. 504–505). Methyl paraben is the safest of the esters. The safety of the esters decreases as the alcohol moiety used increases in number of carbon atoms. Thus ethyl and propyl paraben are less safe than the methyl ester, and the butyl ester is even less safe. However, each of these esters are generally used and are relatively safe. Moreover, microbicidal effect of the esters increases as the number of carbon atoms in the alcohol moiety increases.

It was desired to maximize the microbicidal effect of the paraben esters on gram-negative bacteria and yeasts, and to obtain a kill rate of these microbes which is comparable to that obtained with the gram-positive organisms. This effect was obtained by providing mixtures of methyl and propyl parabens in the compositions of the invention. A further limitation on the effective amount of any single paraben or combination of esters is their limited solubility in water. It has been found for the purposes of the present invention that suitable combinations of dissolved parabens which provide acceptable microbicidal activity are obtained with e.g., 0.005 to 0.5% methyl paraben and 0.005 to 0.1% propyl paraben. One such combination which is presently preferred is about 0.05 to 0.15% of methyl paraben and about 0.02% to 0.05% propyl paraben. Such solutions contain no solid parabens which might be deposited on the eye or objects such as contact lenses to be used in the eye. Such solutions generally are clear rather than cloudy, particularly in the preferred compositions of the present invention.

While such GML solutions may be stable and effective in an anti-microbial sense, in view of the low GML concentrations they are not very effective in a cleaning sense, i.e. in their ability to remove proteinaceous deposits from the surfaces and intersticies of soft lenses.

Generally, these cleaning functions, in solutions for cleaning contact lenses, are carried out by ingredients such as surfactants. While GML has been characterized as having surfactant properties, it is likely that at certain low concentrations achieved by virtue of GML's aqueous solubility above, the surfactancy of GML alone would not be adequate to clean lenses.

It was discovered that the appropriate use of surfactants not only did not interfere with the disinfecting capabilities of the compositions, but in fact could be used to enhance the qualities of the compositions, including forming clear solutions at certain concentrations of ingredients where only cloudy solutions could be achieved without the use of surfactants.

Additionally, it was found that the use of a surfactant not only enhanced the cleaning capabilities of the solution, it also facilitated the solubility of GML and in so doing stabilized the solution. Further indications are that the surfactant functions to augment the anti-microbial activity of some of the anti-microbial agents. It has been found that the judicious use of surfactants described more fully hereinafter, can help to attain stable, non-irritating, effective and, if need be, optically clear aqueous solutions of GML, particularly at concentrations of GML that would not be possible, or not be clear, without the use of surfactants. These other surfactants must themselves meet the stringent requirements of a compound suitable for ophthalmic use.

Therefore, a third, and optional, component of the compositions of the present invention is an organic surfactant. Surfactants fall into four broad classes: anionic, cationic, nonionic and amphoteric. While compounds falling under any of the classes are included within the scope of the present invention, the use of anionic surfactants is preferred. Combinations of anionic, cationic, amphoteric, and nonionic surfactants can also be used, and in particular combinations of an anionic or an amphoteric surfactant with a nonionic surfactant can be used.

The surfactants to be used in the compositions of the present invention must satisfy three criteria. One criterion is solubility, i.e., they must be water soluble at the concentrations at which they are to be used in the compositions of the invention. This criterion is relatively easy to measure and is satisfied by many surfactants. The second criterion is safety, i.e., they must be non-irritating to the eye and non-allergenic for ophthalmic use at the concentrations at which they are to be used in the compositions of the invention. Safety is measured on an acute and chronic basis by standard tests known to the art, such as the Draize eye irritation test. The third criterion to be met is surfactancy, i.e., it is preferable that the compositions be cosmetically acceptable, i.e., that the compositions are clear and remain clear for extended periods. Surfactants are useful to improve the clarity of the solutions of the invention.

It is presently preferred to use an anionic surfactant in relatively low concentrations e.g., 0.005 to 0.15% by weight in the compositions of the invention.

Representative examples of suitable surfactants can be found in *McCutcheon's Emulsifiers & Detergents*, 1983 North American Edition, MC Publishing Co., and include anionic surfactants such as
(1) Hamposyl TM L30 (W. R. Grace Co., Nashua, NH), sodium lauroyl sarcosinate;
(2) Sodium dodecyl sulfate;
(3) Aerosol 413 (American Cyanamid Co., Wayne, NJ), disodium monotallamido-MEA-sulfosuccinate;
(4) Aerosol 200 (American Cyanamid Co.), disodium ethoxylated alkylamide sulfosuccinate;
(5) Lipoproteol TM LCO (Rhodia Inc., Mammoth, NJ), salt of lipo amino acid;
(6) Standapol TM SH 135 (Henkel Corp., Teaneck, NJ), disodium mono-oleamido PEG-2 sulfosuccinate;
(7) Fizul TM 10-127 (Finetex Inc., Elmwood Park, NJ), half ester-sulfosuccinates;
(8) Cyclopol TM SBFA 30 (Cyclo Chemicals Corp., Miami, FL), sulfosuccinate of ethoxylated lauryl alcohol;

amphoterics, such as;
(9) Deriphat TM 170 (Henkel Corp.), N-lauryl myristyl beta amino propionic acid;
(10) Lonzaine TM JS (Lonza, Inc., Fairlawn, NJ), cocoamido sulfobetaine;
(11) Miranol TM C2M-SF (Miranol Chemical Co., Inc., Dayton, NJ), dicarboxylic coconut derivative, disodium salt, salt-free;
(12) Amphoterge TM W2 (Lonza, Inc.), coconut based imidazoline amphoteric, dicarboxylic sodium salt;
(13) Amphoterge TM 2WAS (Lonza, Inc.), modified amphoteric;

non-ionics, such as
(14) Pluronic TM F-68 (BASF Wyandotte, Wyandotte, MI), block copolymers of propylene oxide and ethylene oxide;
(15) Pluronic TM F-127 (BASF Wyandotte), block copolymers of propylene oxide and ethylene oxide;
(16) Brij TM 35 (ICI Americas), polyoxyethylene lauryl ether;
(17) Triton TM X-100 (Rohm and Haas Co., Philadelphia, PA), octylphenoxy polyethoxy ethanol;

(18) Brij ™ 52 (ICI Americas; Wilmington, DE), polyoxyethylene cetyl ether;
(19) Span ™ 20 (ICI Americas), sorbitan monolaurate;
(20) Generol ™ 122 ES (Henkel Corp.), adduct of soya sterol;
(21) Fluorad ™ (3M Co., St. Paul, MN), fluorochemical surfactant;
(22) Triton ™ N-42 (Rohm and Haas Co.,), nonyl phenoxy polyethoxy ethanol;
(23) Triton ™ N-101 (Rohm and Haas Co.), nonyl phenoxy polyethoxy ethanol;
(24) Triton ™ X-405 (Rohm and Haas Co.), octylphenoxy polyethoxy ethanol;
(25) Tween ™ 80 (ICI Americas), sorbitan monooleate-polysorbate 80;
(26) Tween ™ 85 (ICI Americas), sorbitan trioleate (polysorbate 85); and
(27) Brij ™ 56 (ICI Americas), polyoxyethylene cetyl ether.

The preferred compositions of the invention are buffered, isotonic, sterile and optically clear solutions. The compositions are preferably maintained at a pH near that of the eye in order to minimize the risk of irritation if some of the composition contacts the eye. The pH range considered preferable is 4 to 10, and most preferred is from about 5 to 8. This pH is obtained by buffering the composition with a suitable buffering agent such as a phosphate, borate, citric acid or EDTA.

The osmotic strength of the compositions is also controlled to maintain a nearly isotonic solution. This may be done quite readily with commonly available alkali metal salts such as sodium and potassium chlorides. A concentration of about 0.5 to 1.0 weight percent of the composition of sodium chloride would typically be used.

The compositions of the invention can, and preferably should, be sterilized and kept sterile in order to provide optimum anti-microbial activity, and to prevent the contamination of the contact lenses or eyes of the user. Techniques well known in the art would succeed in achieving such sterilization, such as filtration.

Preferably the compositions of the present invention are optically clear, i.e., the user or consumer will be able to see into or through the solution clearly enough to locate a contact lens deposited therein. To achieve this clarity requires that the concentration of components be judiciously controlled relative to each other. An important feature of this invention is that, in light of the nature of compounds involved, the composition is not only stable, effective and safe but also can be kept optically clear.

Various adjuvants may optionally be added to the compositions of the invention to optimize various anti-microbial or cosmetic properties. Many of the compositions of the invention include ethylenediaminetetraacetic acid (EDTA) which, in addition to being useful as a buffering agent, may be utilized as an anti-microbial agent and a chelating agent. As a chelating agent it is known to readily chelate divalent metals such as magnesium and calcium. When used as an anti-microbial or chelating agent it may serve a useful function in the compositions of the invention to chelate such divalent metal ions present in aqueous media to prevent e.g., calcium deposits. It will generally be present in an amount less than 1.0 weight percent of the composition and preferably in an amount of about 0.1%.

Other adjuvants which could optionally be included in the compositions of the invention would be additional anti-microbial agents such as phenoxyethanol, thimerosal, potassium sorbate, chlorhexidine and the like. Each adjuvant added must meet the criteria of water solubility and low eye irritancy when used in the compositions of the invention. For example, phenoxyethanol could be used to increase the microbicidal activity of the compositions, although its limited safety would require the use of relatively low concentrations.

The composition of the invention can be used in various modes with respect to contact lenses. Firstly, the lenses can be rubbed with the composition to remove foreign materials such as proteinaceous and other materials that have been deposited in or on them. Secondly, the lenses can be disinfected by remaining in contact with the composition for a period of at least 4 hours, and preferably overnight, i.e. 6 to 8 hours. When the lenses are removed from the composition they are generally rinsed with a preserved sterile saline solution before being placed back into the eye.

Thirdly, the compositions can be used to preserve or store contact lenses for periods of time on the order of a full day or longer. Generally, when the composition of the invention is intended for use solely in storing or preserving contact lenses, the concentration of anti-microbial ingredients will near the lower limits of the ranges described, compared to when the composition is to be used for cleaning or disinfecting. In this way the composition functions in a microbiostatic rather than a microbicidal fashion, and reduces the absorption of compounds by the lenses over long periods of time, while preventing the proliferation of any microbial growth upon the lenses. Again, before the contact lenses are again placed in the user's eyes they should be disinfected and rinsed as described above.

In order to further illustrate the invention the following examples are provided. These examples should not be construed to limit the invention. Percents given are percent by weight unless otherwise specified.

EXAMPLES 1-8

Compositions were prepared with or without surfactant, and their visual clarity as well as anti-microbial activities were compared. The compositions had the following concentrations of ingredients in deionized water, expressed in percentages of weight to volume;

| Example | Solution Appearance | Surfactant (Hamposyl L-30) | GML | Methyl Paraben | Propyl Paraben | NaCl | EDTA |
|---|---|---|---|---|---|---|---|
| 1 | Hazy | 0.1 | 0.05 | 0.15 | 0.045 | 0.85 | 0.1 |
| 2 | precipitate (not tested) | 0.05 | 0.05 | 0.15 | 0.045 | 0.85 | 0.1 |
| 3 | Clear | 0.05 | 0.01 | 0.15 | 0.045 | 0.85 | 0.1 |
| 4 | Cloudy | | 0.01 | 0.15 | 0.045 | 0.85 | 0.1 |
| 5 | Clear | 0.005 | 0.001 | 0.15 | 0.045 | 0.85 | 0.1 |
| 6 | Cloudy | | 0.001 | 0.15 | 0.045 | 0.85 | 0.1 |
| 7 | Clear | 0.0025 | 0.0005 | 0.15 | 0.045 | 0.85 | 0.1 |

| Example | Solution Appearance | Surfactant (Hamposyl L-30) | GML | Methyl Paraben | Propyl Paraben | NaCl | EDTA |
|---|---|---|---|---|---|---|---|
| 8 | Clear | | 0.0001 | 0.15 | 0.045 | 0.85 | 0.1 |

GML was solvated in a two step process. First a 5% dispersion of GML was prepared by slowly adding with stirring, 5.0 g of GML powder (Lauricidin ™, Med-Chem Laboratories, Monroe, MI) to 80 ml of deionized water at 60°-64° C. After stirring for 10-20 minutes the resultant dispersion was brought to a pH of 7.0-7.2 by either 1N NaOH or 1N HCl, and the solution brought up to a final volume of 100 ml. This dispersion could be stored at room temperature without detectable loss of homogeneity for 1-2 weeks.

To prepare a particular working solution, all of the ingredients except GML were added to deionized water at approximately 80° C., then the solution was allowed to cool to about 60°-65° C. The appropriate volume of the 5% GML dispersion was then added to bring the final concentration of GML to the desired value. After vigorous stirring for 10 minutes, the solution was then brought to the desired pH with 1N NaOH or 1N HCl and the solution was brought up to the final 100 ml volume.

A standard microbicidal assay was performed in which test tubes containing 10 ml each of the solutions was inoculated to a concentration of approximately $1 \times 10^6$ (unless otherwise indicated) microbes per ml.

The tubes were then vortexed and, at designated time intervals after inoculation (exposure times) 0.5 ml aliquots of solution were removed from each tube and transferred to tubes containing 4.5 ml of universal neutralizing medium. This medium contains Tween 80 ™, sodium thioglycolate and lecithin, which neutralize the antimicrobial agents and thereby allow any viable microbes present to grow. These tubes were incubated for a period of time, depending on the type of microbe, appropriate to detect the presence of growth.

The results, set forth in Table I show the presence of microbial growth by the symbol "+", and the absence of growth, i.e. the inhibition or killing of the microbes by the solution tested within the indicated exposure time, by the symbol "−". For instance the first line of data in Table I indicates that solution 1, when subjected to a challenge of $10^6$ organisms/cc, killed all of the organisms when exposed to the organisms for 300 minutes or more, but did not kill them all when exposed for 240 minutes or less.

The results as a whole show that the solutions of Example 4 without surfactant, kills *Staph. epidermidis* in a shorter period of time than the corresponding solution with surfactant. In both cases however the organisms are killed within a period of time suitable for use as a contact lens disinfecting solution.

TABLE I

| Microorganism | Example | \multicolumn{8}{c}{Exposure Time (minutes)} |
|---|---|---|---|---|---|---|---|---|---|

| Microorganism | Example | 15 | 30 | 60 | 120 | 180 | 240 | 300 | 360 |
|---|---|---|---|---|---|---|---|---|---|
| S. epidermidis | 1 | + | + | + | + | + | + | − | − |
| | 3 | + | + | + | + | − | − | − | − |
| | 4 | + | + | + | − | − | − | − | − |
| | 5 | + | + | + | + | + | − | − | − |
| | 6 | + | + | + | − | − | − | − | − |
| | 7 | + | + | + | − | − | − | − | − |
| | 8 | + | + | + | + | + | + | + | − |

TABLE I-continued

| Microorganism | Example | 15 | 30 | 60 | 120 | 180 | 240 | 300 | 360 |
|---|---|---|---|---|---|---|---|---|---|
| S. marcescens | 1 | − | − | − | − | − | − | − | − |
| | 3 | − | − | − | − | − | − | − | − |
| | 4 | − | − | − | − | − | − | − | − |
| | 5 | − | − | − | − | − | − | − | − |
| | 6 | − | − | − | − | − | − | − | − |
| | 7 | − | − | − | − | − | − | − | − |
| | 8 | − | − | − | − | − | − | − | − |
| C. albicans | 1 | − | − | − | − | − | − | − | − |
| | 3 | − | − | − | − | − | − | − | − |
| | 4 | − | − | − | − | − | − | − | − |
| | 5 | − | − | − | − | − | − | − | − |
| | 6 | − | − | − | − | − | − | − | − |
| | 7 | − | − | − | − | − | − | − | − |
| | 8 | + | + | + | + | + | − | − | − |

EXAMPLE 9

The same solutions of Examples 1-8, were tested for microbicidal activity against the fungus *Aspergillus fumigatus* at two concentrations of microbial challenge. $10^3$ Colony Forming Units (CFU) per cc, and at $10^6$ CFU/cc. These tests were run as described in Examples 1-8 except that the incubation time for detection of fungal growth was 14 days at 30°-32° C. The results are set forth in Table II.

The results indicate that, again, the solutions of the invention are effective with or without surfactant, here with respect to killing the $10^3$ CFU/cc challenge of the fungus *A. fumigatus* within a suitable period of time. In this case a solution with surfactant (solution 3) seems to kill the organisms within a shorter period of time than the corresponding solution without surfactant (solution 4).

At the lower challenge concentration, $10^3$ CFU/cc, all of the solutions tested were able to kill the fungus within 1 hour.

TABLE II

| A. fumigatus Challenge | Solution of Example | 15 | 30 | 60 | 120 | 180 | 240 | 300 | 360 |
|---|---|---|---|---|---|---|---|---|---|
| $10^6$ CFU/cc | 1 | + | + | + | + | + | + | + | + |
| | 3 | + | + | + | − | − | − | − | − |
| | 4 | + | + | + | + | + | − | − | − |
| | 5 | + | + | + | + | + | + | + | + |
| | 6 | + | + | + | + | − | − | − | − |
| | 7 | + | + | + | + | + | − | − | − |
| | 8 | + | + | + | + | + | + | + | + |
| $10^3$ CFU/cc | 1 | + | − | − | − | − | − | − | − |
| | 3 | + | − | − | − | − | − | − | − |
| | 4 | + | − | − | − | − | − | − | − |
| | 5 | + | − | − | − | − | − | − | − |
| | 6 | + | + | − | − | − | − | − | − |
| | 7 | + | + | − | − | − | − | − | − |
| | 8 | + | + | − | − | − | − | − | − |

EXAMPLE 10

In order to demonstrate the usefulness of various surfactants in the present invention, several aqueous solutions were prepared. Using a constant GML mixture, the type and concentration of surfactant was varied and each solution tested against *Serratia marcescens.*

GML mixture: 0.05% GML, 0.1% methyl paraben, 0.05% propyl paraben

A. GML mixture plus 0.5% Hamposyl L-30, 0.5% polypropylene glycol P400 (mol. Wt. 400, Matheson, Coleman & Bell Co., Norwood, Ohio).

B. GML mixture plus 1.0% Hamposyl L-30.

C. GML mixture plus 1% Pluronic F-127, 0.5% Hamposyl L-30.

D. GML mixture plus 1% Pluronic F-127, 0.5% Brij 35.

Control solutions: Allergan ™ Cleaning and Disinfecting Solution (Lot No. B1355), Alcon Flex-Care ™ (Lot No. CH 14916)—a rinsing, storage and disinfecting solution for soft lenses containing chlorhexidine and thimerosal.

Separate test tubes containing 10 ml of one of solutions A, B, C and D and control solutions were inoculated to levels of approximately $2 \times 10^6$ microbes per ml with a culture of *Serratia marcescens* ATCC No. 14041.

The tubes were vortexed and at designated time intervals after inoculation (exposure times) 0.5 ml aliquots of solution were removed from each tube and transferred to tubes containing 4.5 ml of universal neutralizing medium. This medium contains Tween 80 ™, sodium thioglycolate and lecithin, which neutralize the antimicrobial agents and thereby allow any viable bacteria present to grow. These tubes were incubated at 37° C. for 24 and 48 hours and checked for the growth of the bacteria. The results are shown in the Table III below wherein "+" indicates bacterial growth, "−" indicates no bacterial growth. The results indicate that solution "A" with the GML mixture and 0.5% Hamposyl ™ killed *Serratia marcescens* in the shortest period of time, i.e. within 10 minutes.

TABLE III

| DIS-INFECTING SOLUTIONS | INCUBATION TIMES | EXPOSURE TIME (Minutes) | | | | | | |
|---|---|---|---|---|---|---|---|---|
| | | 1 | 5 | 10 | 20 | 30 | 60 | 90 |
| A | 24 hours | + | + | − | − | − | − | − |
| | 48 hours | + | + | − | − | (no data) | − | − |
| B | 24 hours | + | + | + | + | − | − | − |
| | 48 hours | + | + | + | + | − | − | − |
| C | 24 hours | + | + | + | + | + | + | − |
| | 48 hours | + | + | + | + | + | + | − |
| D | 24 hours | + | (no data) | + | + | − | − | − |
| Allergan Solution | 24 hours | − | − | − | − | − | − | − |
| | 48 hours | + | (no data) | + | + | − | − | − |
| Alcon Solution | 24 hours | + | − | − | − | − | − | − |
| | 48 hours | + | + | + | − | − | − | − |

EXAMPLE 11

To further demonstrate the alternative surfactants useful in the method and formulations of the invention several aqueous solutions were prepared having the following concentrations of ingredients:

A. 0.025% Cyclopol ™ SBFA 30; 0.05% GML; 0.1% methyl paraben, 0.05% propyl paraben B. 0.05% Hamposyl ™ L-30; 0.05% GML; 0.1% methyl paraben; 0.05% propyl paraben; 0.05% polypropylene glycol C. 0.10% Miranol ™ C2M-SF; 0.05% GML; 0.1% methyl paraben; 0.05% propyl paraben D. 0.025% Cyclopol ™ SBFA 30; 0.05% GML; 0.05% methyl paraben; 0.025% propyl paraben E. 0.05% Hamposyl ™ L-30; 0.05% GML; 0.05% methyl paraben; 0.025% propyl paraben; 0.05% polypropylene glycol F. 0.10% Miranol ™ C2M-SF; 0.05% GML; 0.05% methyl paraben; 0.025% propyl paraben Using several bacteria and the general procedure of Examples 1–8 the results are shown in Table IV wherein "+" indicates microbial growth and "−" indicates no microbial growth. The procedure was varied in that incubation time was 7 days except for the fungus *A. fumigatus* which grows much more slowly than bacteria, where incubation time was 14 days. Each sample was duplicated and in cases where different scores were obtained, both are shown.

Solutions A, B and C, containing higher concentrations of methyl and propyl parabens, were more effective in killing bacteria than solutions D, E and F which had lower concentrations of methyl and propyl parabens. Of the solutions with higher paraben concentrations, i.e. solutions A, B and C, solution A containing Cyclopol ™ and solution B with Hamposyl ™ as the surfactant, appear the most effective.

TABLE IV

| DISINFECTING SOLUTION | MICROORGANISM | EXPOSURE TIMES (Minutes) | | | | | | | |
|---|---|---|---|---|---|---|---|---|---|
| | | 15 | 30 | 60 | 120 | 180 | 240 | 300 | 360 |
| A | S. epidermis | − | − | − | − | − | − | − | − |
| | P. aeruginosa | + | − | − | − | − | − | − | − |
| | S. marcescens | (+/−) | − | − | − | − | − | − | − |
| | C. albicans | + | + | + | + | + | + | (+/−) | − |
| | A. fumigatus | + | + | + | + | + | + | + | + |
| B | S. epidermidis | + | + | (+/−) | (+/−) | (+/−) | (+/−) | − | − |
| | P. aeruginosa | − | − | − | − | − | − | − | − |
| | S. marcescens | − | − | − | − | − | − | − | − |
| | C. albicans | + | + | (+/−) | (+/−) | (+/−) | − | − | − |
| | A. fumigatus | + | + | + | + | + | + | + | + |
| C | S. epidermidis | (−/+) | (−/+) | (−/+) | (−/+) | (−/+) | − | (−/+) | (−/+) |
| | P. aeruginosa | + | − | − | − | − | − | − | − |
| | S. marcescens | − | − | − | − | − | − | − | − |
| | C. albicans | + | + | + | + | + | + | + | + |
| | A. fumigatus | + | + | + | + | + | + | + | + |
| D | S. epidermidis | (−/+) | (−/+) | (−/+) | (−/+) | (−/+) | − | (−/+) | (−/+) |
| | P. aeruginosa | + | (+/−) | + | − | + | − | − | − |
| | S. marcescens | + | + | + | + | + | + | + | + |

TABLE IV-continued

| DISINFECTING SOLUTION | MICROORGANISM | EXPOSURE TIMES (Minutes) | | | | | | | |
|---|---|---|---|---|---|---|---|---|---|
| | | 15 | 30 | 60 | 120 | 180 | 240 | 300 | 360 |
| | C. albicans | + | + | + | + | + | + | + | + |
| | A. fumigatus | + | + | + | + | + | + | + | + |
| E | S. epidermidis | (+/−) | (+/−) | + | + | + | − | (−/+) | (−/+) |
| | P. aeruginosa | + | + | (+/−) | − | − | − | − | − |
| | S. marcescens | + | + | + | + | + | + | + | + |
| | C. albicans | + | + | + | + | + | + | + | + |
| | A. fumigatus | + | + | + | + | + | + | + | + |
| F. | S. epidermidis | (−/+) | (−/+) | − | − | (±/−) | (±/−) | − | − |
| | P. aeruginosa | + | + | + | + | + | (+/−) | (+/−) | + |
| | S. marcescens | + | + | + | + | + | + | + | + |
| | C. albicans | + | + | + | + | + | + | + | + |
| | A. fumigatus | + | + | + | + | + | + | + | + |

EXAMPLE 12

An aqueous solution was prepared with the following concentrations of ingredients: 0.001% GML, 0.005% Hamposyl L-30, 0.15% methyl paraben, 0.045% propyl paraben, 0.85% sodium chloride and 0.1% ethylenediaminetetraacetic acid. The solution was clear, had an osmotic concentration of 288 to 303 milliosmoles and a pH of 7.2 to 7.3. This solution had excellent microbicidal activity. Gram positive organisms were killed in less than 3 hours, gram negative organisms were killed in less than 15 minutes and yeasts were killed in less than 4 hours. The safety of this solution was tested in an acute ocular irritation test in albino rabbits and it was found to be non-irritating.

EXAMPLE 13

To determine the microbicidal activity of GML alone, in water, the following experiment was performed. GML was dispersed in water by heating and stirring a mixture of 5% by weight of GML in water at 60° to 65° C. for 15 to 20 minutes. The final dispersion was adjusted to a pH of 7.0 to 7.5 using 1N sodium hydroxide.

Circular discs (1–2 mm thick×1 cm diameter) of blown microfibrous polyethylene terephthalate web were placed in standard test tubes and saturated with 100 microliters of GML dispersion at concentrations of 0.01%, 0.001%, 0.0001% and 0.00001% and 0.0% (saline control).

A suspension of *Staphylococcus epidermidis* was swabbed onto trypticase soy agar plates and allowed to air dry for several minutes. Excess test solution was expelled from the discs and the discs were then placed centrally on the plates, incubated for 24 hours at 37° C. and scored.

This experiment was repeated three times using separate preparations of the GML solutions. The results are scored as shown in the following Table V as "+" (bacterial growth); "−" (inhibition of bacterial growth) or "±" (here meaning not clearly growth or inhibition, i.e., does not represent alternative results in duplicate samples). The results show that GML alone, dispersed in water, did not inhibit the growth of the gram-positive bacterium, at these concentrations.

TABLE V

| REPETITION NO. | PERCENT GML | | | | |
|---|---|---|---|---|---|
| | 0% | 0.01% | 0.001% | 0.0001% | 0.00001% |
| 1 | + | ± | + | + | + |
| 2 | + | ± | + | + | + |
| 3 | + | ± | + | + | + |

EXAMPLE 14

To determine the minimum concentration of GML that is effective against *Staphylococcus epidermidis*, an aqueous dispersion of GML was prepared by heating and stirring a mixture of 5% by weight of GML in water at 60° to 65° C. for 15 to 20 minutes. This dispersion was used to prepare solutions with the following concentrations:

A. 0.01% Hamposyl L-30, 0.0015% GML, 0.1% methyl paraben, 0.04% propyl paraben, 0.85% sodium chloride and 0.1% ethylenediaminetetraacetic acid.

B. 0.005% Hamposyl L-30, 0.001% GML, 0.1% methyl paraben, 0.04% paraben, 0.85% sodium chloride and 0.1% ethylenediaminetetraacetic acid.

C. 0.0025% Hamposyl L-30, 0.0005% GML, 0.1% methyl paraben, 0.04% propyl paraben, 0.85% sodium chloride and 0.1% ethylenediaminetetraacetic acid.

All solutions were clear at room temperature.

The microbicidal effect of these solutions was tested by inoculating 10 ml of each with suspensions of the bacteria to a final concentration of about $1 \times 10^6$ organisms per milliliter of *Staphylococcus epidermidis* and transferring 0.5 ml aliquots of the bactericidal solution to tubes containing 4.5 ml of universal neutralizing medium after specific exposure times. The tubes of medium were then incubated for 7 days at 37° C. and the results scored as "−" (no bacterial growth) or "+" (bacterial growth), as shown in Table VI.

The results show that the lowest GML concentration tested, i.e., 0.0005% GML, effectively kills *Staphylococcus epidermidis* within 6 hours.

TABLE VI

| SOLUTION | EXPOSURE TIME (Minutes) | | | | | | | |
|---|---|---|---|---|---|---|---|---|
| | 15 | 30 | 60 | 120 | 180 | 240 | 300 | 360 |
| A | + | + | + | + | + | − | − | − |
| B | + | + | + | + | + | − | − | − |
| C | + | + | + | + | + | + | + | − |

EXAMPLE 15

The combined effect of GML and methyl and propyl parabens against *Candida albicans* was demonstrated by the following tests in which the effect of methyl and propyl parabens against *C. albicans* was compared to the effect of GML plus methyl and propyl parabens.

The tests were carried out as described in Example 12 with $2 \times 10^6$ organisms per milliliter being treated with 10 ml of bactericidal solution.

The aqueous solutions used were prepared as follows:
A. 0.10% methyl paraben, 0.050% propyl paraben (boiled to obtain dissolution)
B. 0.10% methyl paraben, 0.050% propyl paraben (heat to 60°-70° C. to mix)
C. 0.050% GML, 0.10% methyl paraben, 0.050% propyl paraben (boiled)
D. 0.050% GML, 0.10% methyl paraben, 0.050% propyl paraben (heated to 60°-70° C.)
E. 0.050% GML (heated to 60°-70° C.)

The results of incubating for 24 hours at 37° C. are shown below in Table VII wherein "+" indicates microbial growth and "−" indicates no microbial growth. Each sample was duplicated and in cases where two scores are shown, one sample differed in activity from its duplicate.

The results show that while neither the solutions containing paraben alone (solutions A and B) nor the solution containing GML alone (solution E) are effective against *C. albicans*, the combination of these ingredients as in solutions C and D will kill the organism within the 6 hours tested.

TABLE VII

| BACTERI-CIDAL SOLUTION | EXPOSURE TIME (Minutes) | | | | | | | |
|---|---|---|---|---|---|---|---|---|
| | 15 | 30 | 60 | 120 | 180 | 240 | 300 | 360 |
| A | + | + | + | + | + | + | + | + |
| B | + | + | + | + | + | + | + | + |
| C | + | + | + | + | + | +/− | − | − |
| D | + | + | + | + | + | + | − | −/+ |
| E | + | + | + | + | + | + | + | + |

EXAMPLE 16

Using the method of Example 1 a microbicidal solution of 0.05% GML, 0.05% Hamposyl L-30, 0.1% methyl paraben, 0.05% propyl paraben, 0.05% polypropylene glycol and 0.1% ethylenediaminetetraacetic acid was prepared and its effect against various microbes was tested. The results are shown as averages of duplicates in Table VIII below wherein "+" indicates microbial growth, "−" indicates inhibition and "+/−" indicates that duplicates differed in activity.

TABLE VIII

| | EXPOSURE TIMES (Minutes) | | | | | | | |
|---|---|---|---|---|---|---|---|---|
| | 15 | 30 | 60 | 120 | 180 | 240 | 300 | 360 |
| S. epidermidis | − | − | − | − | − | − | − | − |
| P. aeruginosa | − | − | − | − | − | − | − | − |
| S. marcescens | − | − | − | − | − | − | − | − |
| C. albicans | − | − | − | − | − | − | − | − |
| A. fumigatus | + | + | + | + | (−/+) | − | − | − |

This experiment demonstrates the microbicidal effectiveness of a solution of the invention against all microorganisms required for FDA testing including the fungus *A. fumigatus*.

EXAMPLE 17

The extent of absorption of ingredients from a disinfecting solution of the invention by a soft contact lens material (made of polymerized hydroxyethyl methacrylate) was measured.

Four discs of hydroxyethyl methacrylate (12.75 mm diameter, 0.2 mm thickness) were soaked for eight days in 5 ml of an aqueous solution containing:
0.112% Hamposyl L-30
0.05% GML
0.10% methyl paraben
0.05% propyl paraben
0.8% sodium chloride
0.1% ethylenediaminetetraacetic acid The discs were then extracted for about 16 hours with excess pyridine. The pyridine extracts were evaporated to dryness, treated with excess N,O-bis(trimethylsilyl)trifluoroacetamide containing 1% trimethylchlorosilane to derivatize and heated to 100° C. The solutions were analyzed by capillary gas chromatography for the presence of derivatives of the ingredients of the disinfecting solution. Table IX indicates the average amount of each ingredient that was absorbed by a soft contact lens after soaking for 8 days.

TABLE IX

| Ingredient | Average Concentration per Lens (mg) |
|---|---|
| methyl paraben | 0.09 |
| propyl paraben | 0.10 |
| GML | 0.006 |
| Hamposyl L-30 | 0.05 |
| Ethylenediaminetetraacetic acid | 0.00 |

In the Draize ocular irritation test it had been found that all of the ingredients of the disinfecting solution were non-irritating as shown in Table X below when 0.1 ml of solution was placed in the eye of rabbits:

TABLE X

| Ingredient | Concentration (mg/100 ml) | Concentration (mg/eye) |
|---|---|---|
| methyl paraben | 100 | 0.1 |
| propyl paraben | 50 | 0.05 |
| GML | 50 | 0.05 |
| Hamposyl L-30 | 50 | 0.05 |

The results indicate that the amount of ingredients that should be absorbed by a contact lens, even if eluted by the lens into the eye, should not be irritating to the eye.

EXAMPLE 18

The minimum effective concentration of GML was shown to vary with the initial concentration of microorganisms used to challenge the disinfecting solution. Each of the following test solutions was challenged with *Staphylococcus epidermidis* and *Candida albicans* at the inoculum concentrations of $10^6$ and $10^3$ organisms/ml solution as described in Example 1. The ingredients of the solutions are listed as weight percentages of the following ingredients, in order; surfactant (H-refers to Hamposyl L-30), GML, methyl paraben, propyl paraben, $N_aCl$, EDTA.

| | Hamposyl L-30 | GML | Methyl Paraben | Propyl Paraben | NaCl | EDTA |
|---|---|---|---|---|---|---|
| A | 0.005 | 0.001 | 0.15 | 0.045 | 0.85 | 0.1 |
| B | 0.0025 | 0.0005 | 0.15 | 0.045 | 0.85 | 0.1 |
| C | 0.001 | 0.0001 | 0.15 | 0.045 | 0.85 | 0.1 |
| D | Allergan Control of Example 10. | | | | | |

-continued

| | Hamposyl L-30 | GML | Methyl Paraben | Propyl Paraben | NaCl | EDTA |
|---|---|---|---|---|---|---|
| E | Alcon Control of Example 10 | | | | | |

The results are shown in Table XI.

TABLE XI

| | | \multicolumn{8}{c}{EXPOSURE TIME (Minutes)} |
|---|---|---|---|---|---|---|---|---|---|
| | | 15 | 30 | 60 | 120 | 180 | 240 | 300 | 360 |
| Staph. epidermidis ($10^6$/cc) | A | + | + | + | + | + | + | − | − |
| | B | + | + | + | + | + | + | + | + |
| | C | + | + | + | + | + | + | + | + |
| | D | − | − | − | − | − | − | − | − |
| | E | − | − | − | − | − | − | − | − |
| Staph. epidermidis ($10^3$/cc) | A | + | + | + | + | − | − | − | − |
| | B | + | + | + | + | − | − | − | − |
| | C | + | + | + | + | + | + | + | + |
| | D | + | + | + | + | + | + | − | − |
| | E | − | − | − | − | − | − | − | − |
| Candida albicans ($10^6$/cc) | A | + | + | − | − | − | − | − | − |
| | B | + | + | + | − | − | − | − | − |
| | C | + | + | + | + | + | + | − | − |
| | D | + | + | + | − | − | − | − | − |
| | E | + | − | − | − | − | − | − | − |
| Candida albicans ($10^3$/cc) | A | + | − | − | − | − | − | − | − |
| | B | + | − | − | − | − | − | − | − |
| | C | + | + | + | + | + | + | + | − |
| | D | + | − | − | − | − | − | − | − |
| | E | − | − | − | − | − | − | − | − |

The results indicate, for example, that while 0.001% GML kills this inoculum in 6 hours, however 0.0005% will kill an inoculum of $10^3$/cc organisms in 3 hours, as will 0.001% GML. Similar results are seen with respect to *Candida albicans*.

What is claimed is:

1. An aqueous ophthalmic composition, which is non-irritating to the eyes, for cleaning, disinfecting or preserving contact lenses comprising
   (a) water;
   (b) an effective amount of up to 0.1% by weight of a first anti-microbial agent consisting essentially of a polyol ester having a formula selected from

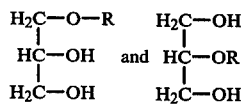

where R is the residue of lauric acid; and
   (c) an effective amount of a second anti-microbial agent comprising one or more esters of para-hydroxybenzoic acid.

2. An aqueous solution according to claim 1.

3. A buffered, sterile, and isotonic composition according to claim 1.

4. An optically clear composition according to claim 2 or 3.

5. A composition according to claim 1 wherein said second anti-microbial agent comprises a mixture of the methyl ester of para-hydroxybenzoid acid and the propyl ester of para-hydroxybenzoid acid.

6. A composition according to claim 5 wherein said mixture comprises from about 0.005 to 0.3% by weight of said composition of the methyl ester of para-hydroxybenzoic acid and from about 0.005 to 0.1% by weight of said composition of the propyl ester of para-hydroxybenzoic acid.

7. A composition according to claim 1 further comprising an organic surfactant.

8. A solution according to claim 7.

9. A buffered, sterile and isotonic composition according to claim 7.

10. An optically clear composition according to claim 8 or 9.

11. A composition according to claim 7 wherein said second anti-microbial agent comprises a mixture of the methyl ester of para-hydroxybenzoic acid and the propyl ester of para-hydroxybenzoid acid.

12. A composition according to claim 11 wherein said mixture comprises from about 0.005 to 0.3% by weight of said composition of the methyl ester of para-hydroxybenzoic acid and from about 0.005 to 0.1% by weight of said composition of the propyl ester of para-hydroxybenzoic acid.

13. A composition according to claim 7 wherein said surfactant is anionic.

14. A composition according to claim 7 wherein said surfactant is present in an amount effective to maximize the solubility of said first anti-microbial agent.

15. A composition according to claim 7 wherein said surfactant is present in an amount from about 0.005 to 0.15% by weight of said composition.

16. A composition according to claim 1 or 7 further comprising ethylenediaminetetraacetic acid.

17. A method of cleaning contact lenses comprising rubbing said lenses with the aqueous composition of claim 1 or 7 and rinsing said lenses for a time sufficient to remove foreign material from said lenses.

18. A method of disinfecting contact lenses comprising contacting said lenses with said aqueous composition of claim 1 or 7 for a time sufficient to kill microorganisms on said lenses.

19. A method of preserving contact lenses comprising contacting said lenses with said aqueous composition of claim 1 or 7 for a time sufficient to inhibit microorganism growth on said lenses.

20. A composition according to claim 1 wherein the pH of said composition is from about 4 to 10.

21. A composition according to claim 20 wherein said pH is from about 5 to 8.

22. An aqueous ophthalmic composition, which is non-irritating to the eyes, for cleaning, disinfecting or preserving contact lenses comprising
   (a) at least 99% water;
   (b) 0.0001 to 0.1% by weight of a first anti-microbial agent consisting essentially of a polyol ester having a formula selected from

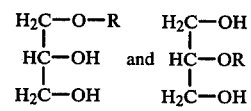

where R is the residue of lauric acid.
   (c) 0.02 to 0.2% of a second antimicrobial agent comprising one or more esters of para-hydroxybenzoic acid; and
   (d) 0 to 0.15% of an organic surfactant,
said composition having a pH of from about 5 to 8.

* * * * *

UNITED STATES PATENT AND TRADEMARK OFFICE
CERTIFICATE OF CORRECTION

PATENT NO. : 4,485,029
DATED : November 27, 1984
INVENTOR(S) : Kenneth H. Kato and Arlene J. Mencke It is certified that error appears in the above—identified patent and that said Letters Patent is hereby corrected as shown below:

Col. 4, line 56, "acit" should read -- acid -- .
Col. 9, line 12, "64°" should read -- 65° -- .
Col. 11, line 53, "S. epidermis" should read
-- S. epidermidis -- .
Col. 14, line 37, after "0.04%" insert -- propyl -- .
Col. 17, line 61, "para-hydroxybenzoid" should read
-- para-hydroxybenzoic -- .
Col. 18, line 13, "para-hydroxybenzoid" should read
-- para-hydroxybenzoic -- .

Signed and Sealed this

Twenty-third Day of July 1985

[SEAL]

Attest:

DONALD J. QUIGG

Attesting Officer    Acting Commissioner of Patents and Trademarks